United States Patent
Ishii et al.

(10) Patent No.: US 6,959,105 B1
(45) Date of Patent: Oct. 25, 2005

(54) FINGERPRINT IDENTIFICATION DEVICE EQUIPPED WITH A USER RECORDING UNIT

(75) Inventors: Hirotaka Ishii, Kyoto (JP); Takeo Morita, Kyoto (JP); Yasuhide Yomo, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/450,757

(22) Filed: Nov. 30, 1999

(30) Foreign Application Priority Data

Dec. 29, 1998 (JP) .................................. 10-377135

(51) Int. Cl.⁷ ........................... G06K 9/00; G06K 9/46; B42D 15/00; G05B 19/00
(52) U.S. Cl. ........................ 382/124; 382/190; 283/68; 340/5.52
(58) Field of Search ................................ 382/124, 125, 382/115, 116, 190, 192; 283/68; 356/71; 340/5.52

(56) References Cited

U.S. PATENT DOCUMENTS

| | | | |
|---|---|---|---|
| 4,186,378 A * | 1/1980 | Moulton ...................... 356/71 |
| 4,210,899 A * | 7/1980 | Swonger et al. .......... 340/5.53 |
| 4,246,568 A * | 1/1981 | Peterson ..................... 382/126 |
| 4,817,183 A * | 3/1989 | Sparrow ..................... 382/125 |
| 5,465,303 A * | 11/1995 | Levison et al. ............. 382/124 |
| 5,594,646 A * | 1/1997 | Itoh et al. ..................... 701/35 |
| 5,796,355 A | 8/1998 | Smigelski ..................... 311/33 |
| 5,959,541 A * | 9/1999 | DiMaria et al. ........... 340/5.52 |
| 5,995,014 A * | 11/1999 | DiMaria ..................... 340/5.52 |
| 6,175,640 B1 * | 1/2001 | Wada .......................... 382/124 |
| 6,185,318 B1 * | 2/2001 | Jain et al. ................... 382/115 |

FOREIGN PATENT DOCUMENTS

| | | |
|---|---|---|
| EP | 0 568 342 | 11/1993 |
| GB | 1 548 667 | 7/1979 |
| GB | 2 241 064 | 8/1991 |
| WO | WO 93/10614 | 5/1993 |
| WO | 98/35118 | 8/1998 |
| WO | 98/52146 | 11/1998 |

* cited by examiner

*Primary Examiner*—Mehrdad Dastouri
(74) *Attorney, Agent, or Firm*—Foley & Lardner LLP (57) ABSTRACT

A fingerprint identification device to identify fingerprints is equipped with a fingerprint reader unit to input a fingerprint to be detected and a database unit to record a fingerprint database which is provided in advance. A fingerprint comparing unit identifies the input fingerprint via the fingerprint reader unit by comparing with the fingerprint database recorded in the database unit and a user recording unit records the input fingerprint input by the fingerprint reader unit.

9 Claims, 7 Drawing Sheets

FINGERPRINT IDENTIFICATION DEVICE EQUIPPED WITH A USER RECORDING UNIT

FIELD OF THE INVENTION

This invention relates to a fingerprint identification device which can discriminate between different individuals by their fingerprints. Specifically, the fingerprint identification device according to present invention is equipped with a user recording unit. The user recording unit records the fingerprint of users for the purpose of the maintenance, repair or for providing higher security.

BACKGROUND OF THE INVENTION

Figure 1:
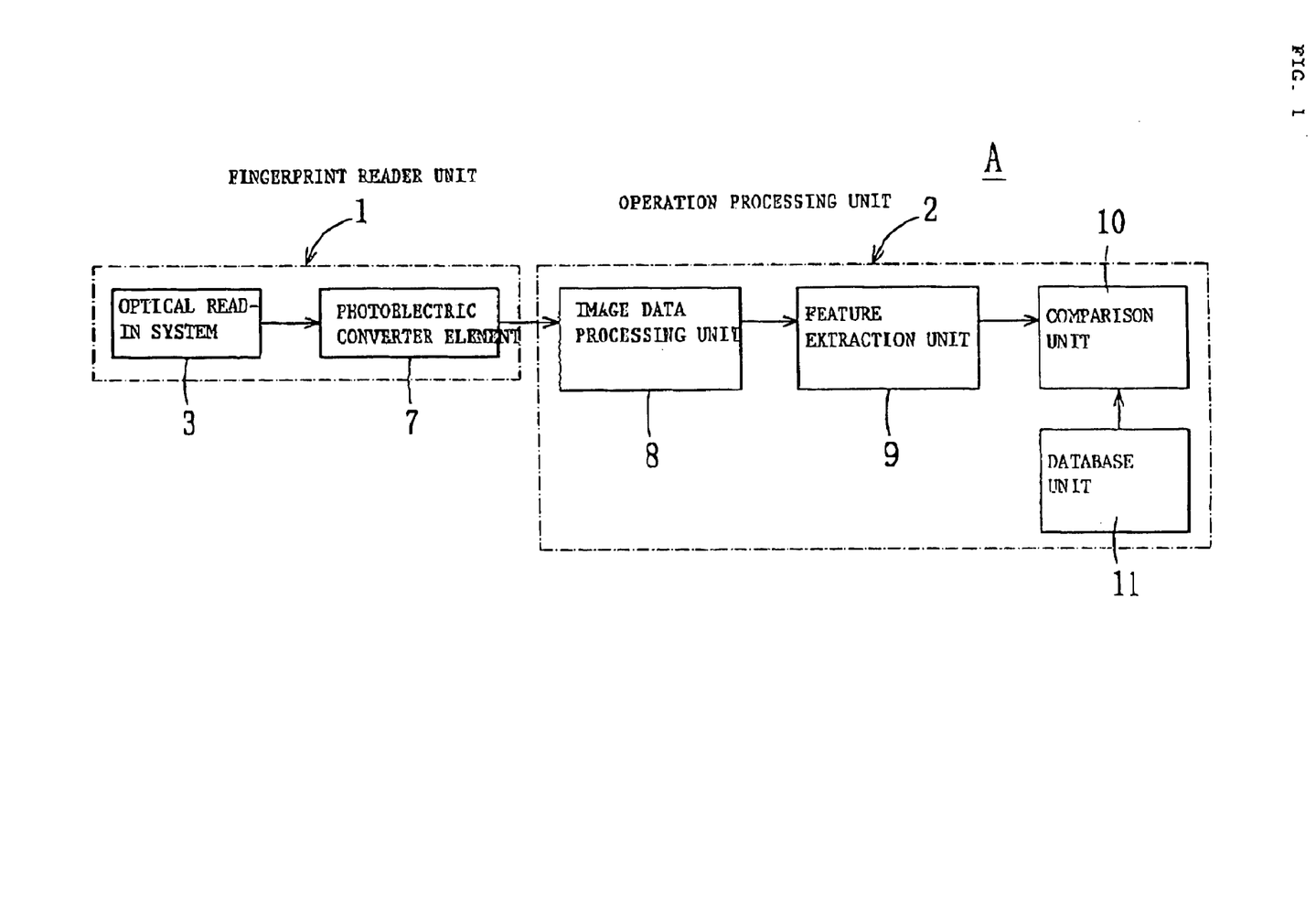
FIG. 1 is a block diagram of a prior art fingerprint identification device to identify fingerprints.

FIG. 1 is a block diagram of a prior art finger identification device A to verify fingerprints. Fingerprint identification device A includes a fingerprint reader unit 1 including an optical read-in system 3 and a photoelectric converter element 7, and an operation processing unit 2.

Figure 2:
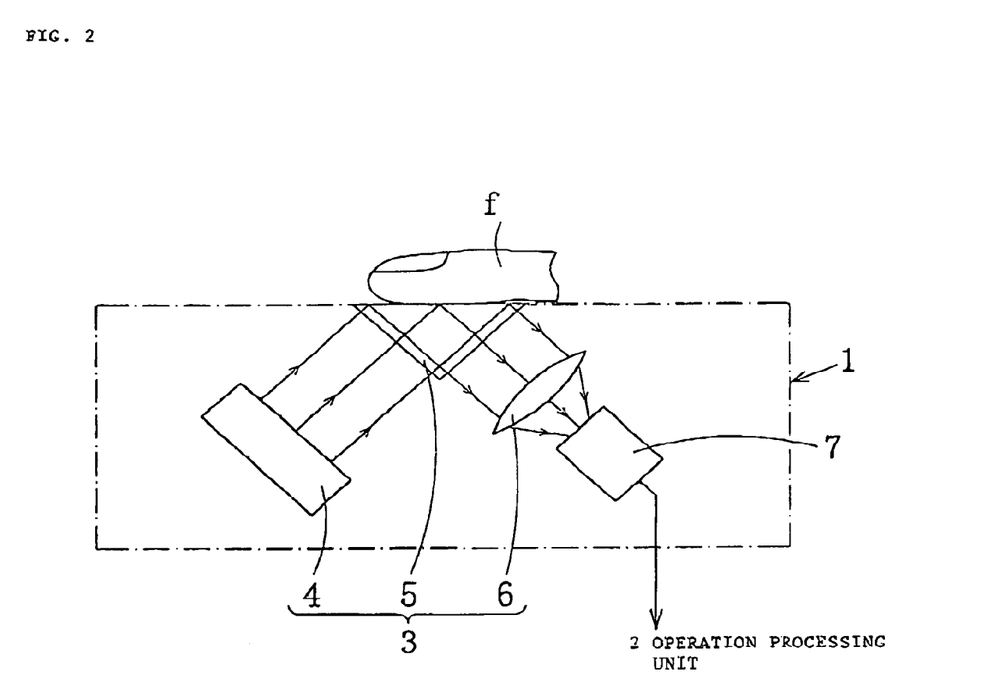
FIG. 2 is a sketch of a fingerprint reader unit.

FIG. 2 shows a configuration of the fingerprint reader unit 1. Optical read-in system 3 consists of a light source 4, such as a light-emitting diode or the like; a triangular prism 5, to which a person's finger f is applied, and which selectively emits light in an optical pattern corresponding to the pattern of the fingerprint; and a condensing lens 6. Photoelectric converter element 7 generates binary electrical signals which correspond to the optical pattern focussed by condensing lens 6. The photoelectric converter element 7 might, for example, consist of a Charge Coupled Device (CCD).

In the fingerprint reader unit 1, when a finger f, which is the object of investigation, is placed on the oblique surface of the prism 5, the light from the light source 4 which enters the prism 5 is totally reflected by the surface of the prism in conjunction with the grooves of the fingerprint (or print). This reflected light travels toward the lens 6. At the ridges of the print, the light passes through the oblique surface of prism 5 and is scattered by the print. In other words, the light is totally reflected by the grooves of the fingerprint and creates the light portion of the image, while the light is scattered by the ridges of the print and creates the dark portion of the image. The light from light source 4 is thus selectively reflected by the oblique surface of prism 5 in a pattern of light and dark portions which exactly matches the fingerprint pattern. The optical pattern of light and dark portions which is reflected by prism 5 is condensed by the condensing lens 6 and focussed on the photoelectric converter element 7. The optical pattern focussed on element 7 is converted by element 7 into binary electrical signals which are then output, as image data representing the pattern of the fingerprint, to the operation processing unit 2.

As can be seen in FIG. 1, the operation processing unit 2 consists of an image data processing unit 8, a feature extraction unit 9, a comparison unit 10 and a database unit 11. Image data processing unit 8 executes various processing routines such as correcting and compressing the image data transmitted from photoelectric converter element 7. Based on a specified algorithm known to those skilled in the art, feature extraction unit 9 extracts features from the fingerprint pattern (i.e., the image data) processed by image data processing unit 8. For example, it might use the scheme disclosed in Japanese Patent publication 5-54129. Database unit 11 records, prior to use, the fingerprint data (e.g., the feature count) for legitimate or authorized users of the device. Comparison unit 10 compares the fingerprint data (e.g., the feature count) extracted by feature extraction unit 9 with the data (or count) for the authorized users which are recorded in the database unit 11 and determines whether or not they match.

If comparison unit 10 determines that the fingerprint data matches, it outputs judgment data indicating that the match was successful, and a specified operation is executed (for example, the door is unlocked and the person is granted entry, or the car engine is started). If the match is not successful, comparison unit 10 outputs judgment data indicating that it has failed to find a match, and the specified operation is prevented.

With this sort of fingerprint identification device, it sometimes occurs that judgment data indicating a successful match is not output even though the user whose finger is on the read-in unit is an authorized user. In this case, the specified operation is prevented. If this sort of failure occurs frequently, the device needs to be repaired, and someone needs to ascertain where the malfunction is occurring.

Failures of this sort may be due to a number of causes. The prism of the read-in unit may be scratched; the person's finger may be dirty; or there may be foreign matter stuck to the read-in unit or the finger. If any of these things happen, they may cause a problem in the data compression routine used by the image data processing unit to compress the fingerprint pattern, or the features which distinguish one individual's pattern from another's may be difficult to extract, or a problem may occur in the comparison program.

Therefore, such prior art devices to identify fingerprints require much time and effort to determine the cause and the location of a malfunction before any repairs could be made.

SUMMARY OF THE INVENTION

The present invention was developed, inter alia, to solve the problems discussed above. One of the objective of the present invention is to provide a fingerprint identification device to identify fingerprints which, when malfunctioning, readily allows the location of the malfunction to be ascertained relatively simply.

The fingerprint identification device to identify fingerprints according to the present invention is equipped with: 1) a fingerprint reader unit to input a fingerprint to be detected; 2) a database unit to record a fingerprint database which is provided in advance; 3) a fingerprint comparing unit to identify the input fingerprint input by the fingerprint reader unit by comparing with the fingerprints in the fingerprint database recorded in the database unit; and 4) a user recording unit that records the input fingerprint input by the fingerprint reader unit.

When the fingerprint data input via the aforesaid reader unit is compared with the fingerprint data recorded in the database unit, the input fingerprint data is also recorded in the user recording unit.

The term "fingerprint data" means either the raw fingerprint pattern or processed data resulting when the raw data is processed to extract pertinent features. The raw fingerprint pattern may be the optical pattern of the fingerprint as read optically, the electrical pattern achieved by converting the optical pattern to electrical signals, the data resulting from compressing the electrical pattern, or other similar data generally capable of being substantially restored to the original fingerprint. The processed data is not limited to data representing features extracted from the original image, but may include data from which the original image cannot be fully restored.

The fingerprint identification device to identify fingerprints disclosed above provides that the fingerprint data input via the reader unit be stored. When a malfunction occurs, a user can try to access the fingerprint data and in this way ascertain whether the cause of the problem is in the step prior to obtaining the data or subsequent to it. This will help determine the source of the malfunction. This design thus makes it easier to ascertain the location of a malfunction when doing inspections or repairs.

All fingerprint data are stored when someone touches the fingerprint reader unit. It also happens when an unauthorized person attempts to touch the reader unit in order to gain access. This provides a psychological deterrent effect. If the fingerprint identification device is installed in a car or on the door of a building, it will prevent the car from being stolen or deter any unauthorized person from entering the building without permission.

Another aspect of the fingerprint identification device to identify fingerprints provides that the fingerprint data input via the aforesaid reader unit is recorded in the aforesaid user recording unit only when the fingerprint data which have been input does not match those which are already stored in the database unit.

Since in fact the only time a user's fingerprint data needs to be saved is when the match is unsuccessful, choosing this expedient allows economies to be realized in the memory capacity of the user recording unit. This also make it less likely that the memory of the user recording unit will fill up so that fingerprint data can no longer be recorded.

Yet another aspect of fingerprint identification device to identify fingerprints provides that the fingerprint data recorded in the aforesaid user recording unit is data representing raw data of the fingerprint which is input via the fingerprint reader unit.

In this embodiment, the fingerprint pattern (i.e., the optical pattern, the electrical pattern, the compressed data, etc.) is recorded in the user recording unit. This allows a greater quantity of fingerprint data to be used and enables the user to make a detailed diagnosis of the location and cause of a malfunction. And since the fingerprint itself can be restored, the fingerprint identification device can be particularly effective in preventing car theft or unauthorized entry to a building.

Still another aspect of fingerprint identification device to identify fingerprints provides that the fingerprint data recorded in the aforesaid user recording unit includes a feature count extracted from the fingerprint pattern input via the fingerprint reader unit.

In this embodiment, only the data representing the feature count extracted from the fingerprint pattern is saved. As a result, only a small quantity of data needs to be saved in the user recording unit. This allows the memory capacity in the user recording unit to be put to its best use.

Yet another aspect of fingerprint identification device provides that the user recording unit records a recording history along with the fingerprint data input via the reader unit. This recording history could include a variety of data according to a user's needs, such as the date and time the fingerprint was recorded or the power supply voltage at that time.

Since this embodiment saves the recording history along with the fingerprint data, the user can investigate the cause of a malfunction by referring to the date and time that the fingerprint identification device first showed signs of trouble. Recording the date in a recording history also is an effective deterrent to car theft and unauthorized entry by providing additional information about the car theft or unauthorized entry.

BRIEF DESCRIPTION OF THE DRAWINGS

The accompanying drawings, which are incorporated in and constitute a part of the specification, illustrate presently preferred embodiments of the invention, and, together with the general description given above and the detailed description of the preferred embodiments given below, serve to explain the principles of the invention.

DETAILED DESCRIPTION OF THE PREFERRED EMBODIMENTS

Figure 3:
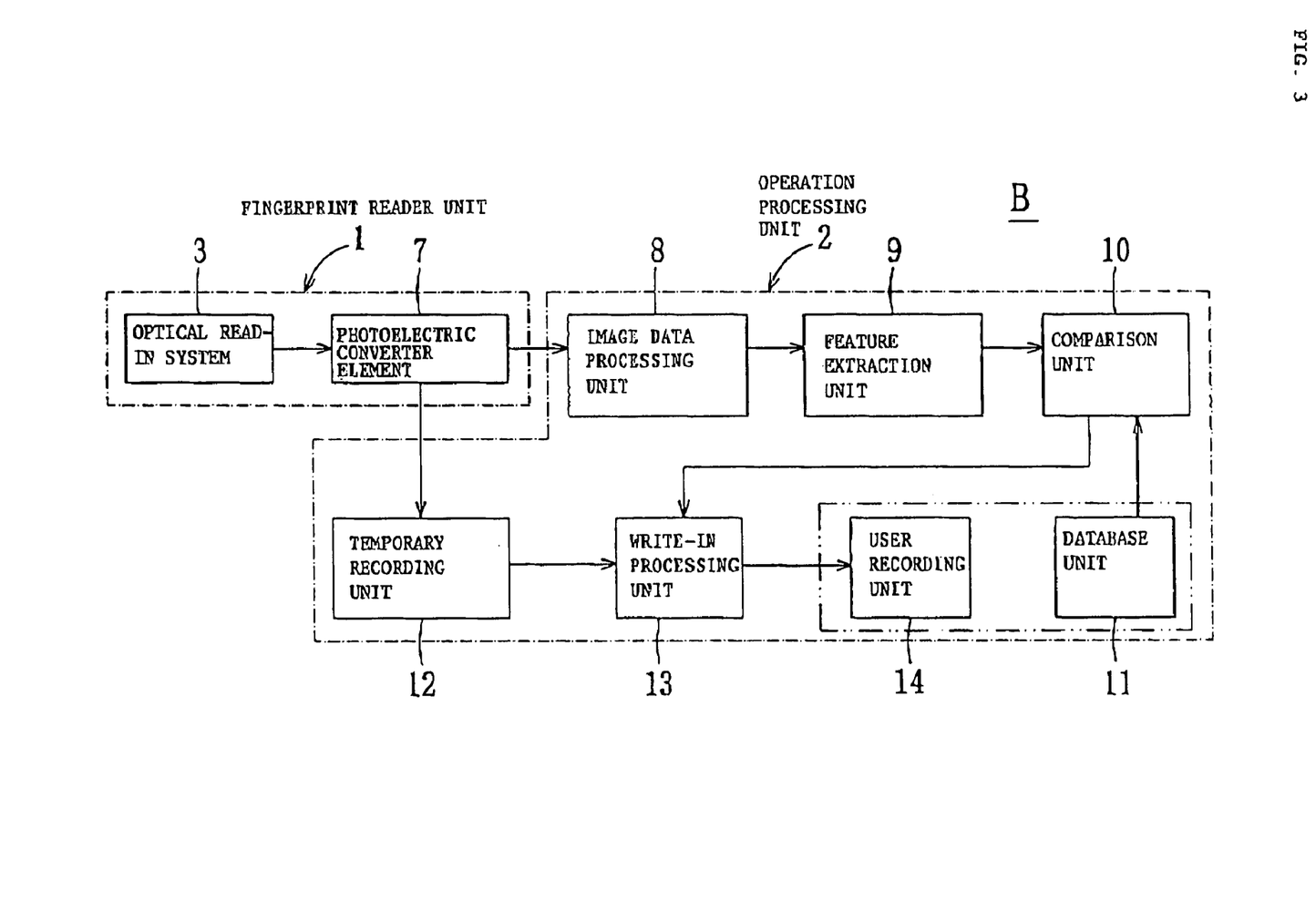
FIG. 3 is a block diagram of a fingerprint identification device to identify fingerprints according to a first preferred embodiment of this invention.

FIG. 3 is a block diagram of a fingerprint identification device B to identify fingerprints, according to the first preferred embodiment of this invention. Fingerprint identification device B consists of a fingerprint reader unit 1 and an operation processing unit 2. Fingerprint reader unit 1 consists of an optical reading system 3 and a photoelectric converter element 7. An actual appearance of the fingerprint identification device is as shown in FIG. 2. When the person places his finger on optical reading system 3, his fingerprint pattern is read optically. This optical fingerprint pattern is converted by photoelectric converter element 7, such as a CCD or the like, to binary electrical signals (i.e., to image data) and output.

Operation processing unit 2 includes an image data processing unit 8, a feature extraction unit 9, a comparison unit 10, a database unit 11, a temporary recording unit 12, a write-in processing unit 13 and a user recording unit 14. Database unit 11 consists of a writable non-volatile memory such as an Electrically Erasable Programmable Read-Only Memory (EEPROM). Data concerning feature counts extracted from the fingerprint patterns of authorized users (hereafter, "feature count data") are stored prior to use in database unit 11. The recording scheme is not discussed in detail, but can be implemented by, for example, a person pressing his finger on fingerprint reader unit 1 while the fingerprint identification device is in a recording mode. Image data processing unit 8 and feature extraction unit 9 extract a feature count, and the resulting feature count data are stored in the database unit 11.

Temporary recording unit 12 consists of an inexpensive, erasable volatile memory such as a RAM. When the person presses his finger on fingerprint reader unit 1 and his fingerprint is read, the fingerprint pattern output by photoelectric converter element 7 in the fingerprint reader unit 1 (i.e., the image data) is temporarily saved.

When photoelectric converter element 7 outputs the fingerprint pattern to image data processing unit 8, the image data processing unit 8 executes various processing routines such as adjustment or compression routines on the fingerprint pattern (i.e., on the image data). Feature extraction unit 9 extracts a feature count from the fingerprint pattern processed by the image data processing unit 8 according to a specified algorithm. The feature count data extracted in this way by feature extraction unit 9 are transmitted to comparison unit 10. Comparison unit 10 reads out feature count data stored in database unit 11 and compares them with the feature count data from the current fingerprint to see if they match.

If the feature count data matches, comparison unit 10 outputs judgment data indicating that the match is successful, and transmits a signal indicating the same to write-in processing unit 13. When it receives the "match successful" signal from comparison unit 10, the write-in processing unit 13 does not execute any processing. Alternatively, it would also be acceptable for comparison unit 10 not to send a signal to write-in processing unit 13 in case the match is successful.

If the feature count data does not match, comparison unit 10 outputs judgment data indicating that the match is unsuccessful, and transmits a signal indicating the same to write-in processing unit 13. When it receives the "match unsuccessful" signal from the comparison unit 10, the write-in processing unit 13 transmits the fingerprint pattern stored in temporary recording unit 12 to the user recording unit 14, where it is stored.

User recording unit 14 consists of a writable non-volatile memory such as an EEPROM. The fingerprint pattern stored in the user recording unit 14 is saved until an erasing routine is executed. If the fingerprint pattern is stored in user recording unit 14 when the match is unsuccessful but not when it is successful, the memory can be used economically. The fingerprint pattern recorded in temporary recording unit 12 can be erased when the next pattern is written over it.

User recording unit 14 and database unit 11 may be two separate memories, or they may be a single memory divided into two regions. Write-in processing unit 13 includes a programmed microprocessor (a CPU). A single microprocessor may serve as the processing unit 13, the image data processing unit 8, the feature extraction unit 9 and the comparison unit 10.

In this fingerprint identification device B to identify fingerprints, if the fingerprint data read by fingerprint reader unit 1 does not match any of the stored fingerprints, the fingerprint pattern output by unit 1 is stored in user recording unit 14. Thus if the match is unsuccessful, even though the fingerprint pattern that is input belongs to an authorized user, the location of the malfunction can be narrowed down. In this embodiment, therefore, since the fingerprint pattern output by photoelectric converter element 7 is stored in the user recording unit 14, it can be restored in the event of a malfunction. This allows the user to determine whether the malfunction occurred in the fingerprint reader unit 1 or the operation processing unit 2, thus simplifying the investigation.

In this embodiment, also, because the fingerprint pattern read by fingerprint reader unit 1 is stored in database unit 11, any pattern that is read can be restored in detail. This allows the pattern to be studied carefully.

With the fingerprint identification device B to identify fingerprints of the first embodiment, if the feature count data does not match a stored fingerprint feature data, the fingerprint pattern is stored in user recording unit 14. This is an effective theft deterrent if the fingerprint identification device is installed in a car. To enhance this effect, a sign might be displayed in the car indicating that fingerprints which do not match those of an authorized driver will be stored, and an alarm could sound when the prints do not match.

Figure 4:
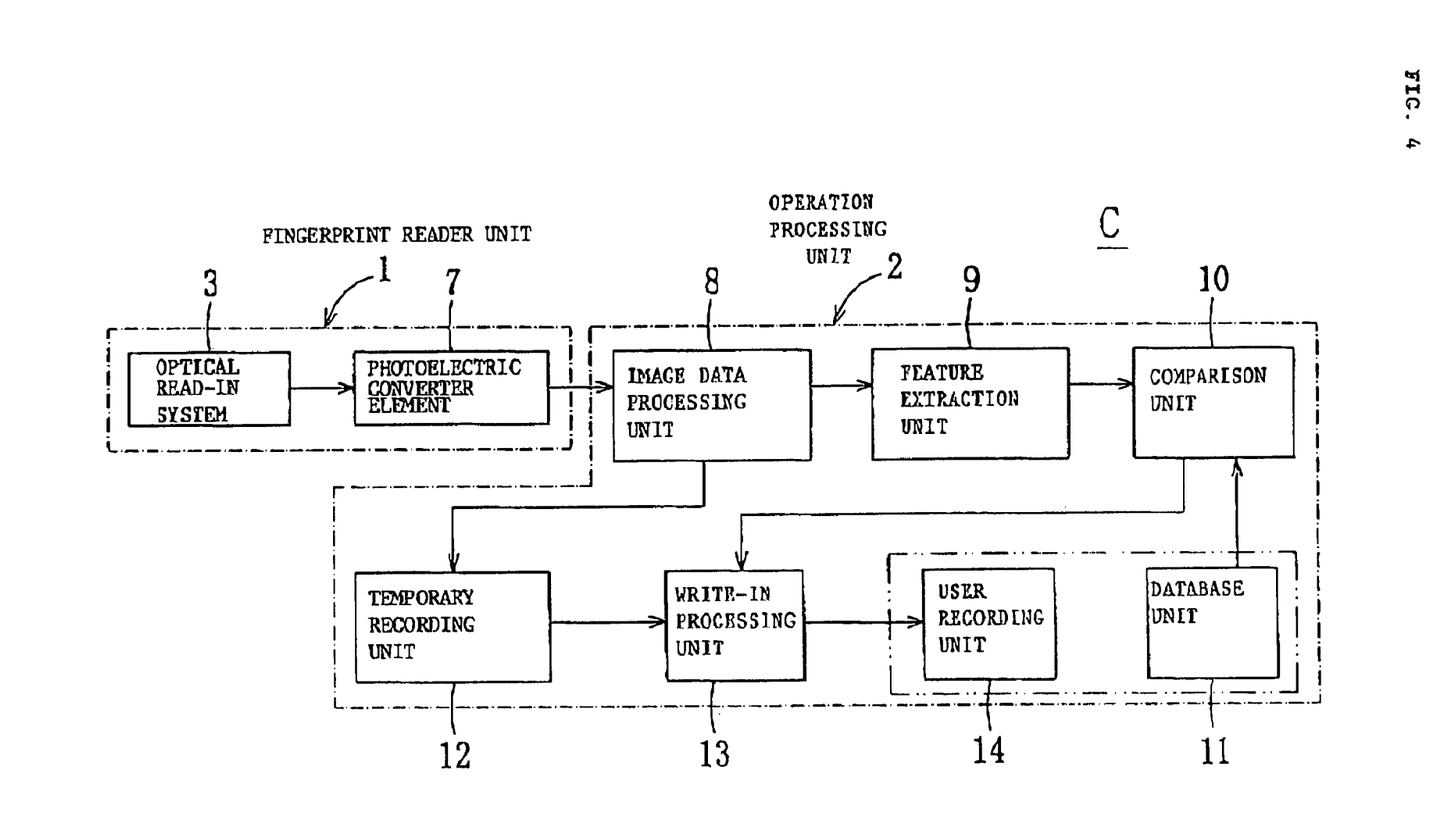
FIG. 4 is a block diagram of another fingerprint identification device to identify fingerprints according to a second preferred embodiment of this invention.

FIG. 4 is a block diagram of a fingerprint identification device C to identify fingerprints according to a second preferred embodiment of this invention. In the fingerprint identification device C, the fingerprint pattern (or image pattern) resulting from the adjustment or compression routines executed by image data processing unit 8 is stored in the temporary recording unit 12. If the match is unsuccessful, this pattern is saved in the user recording unit 14.

In this embodiment, the fingerprint pattern stored in user recording unit 14 consists of the compressed data processed by image data processing unit 8. The use of compressed data further reduces the consumption of user recording unit 14. Also, with this embodiment, the user can determine in the case of a malfunction whether the problem is visible in the pattern before the feature count is extracted by feature extraction unit 9 or whether it showed up in the data after the feature count is extracted. This simplifies the investigation of malfunctions. Furthermore, the compressed image data can be readily restored to the original image (i.e., the fingerprint pattern), so this embodiment has the same theft-deterrent effect as the first embodiment.

Figure 5:
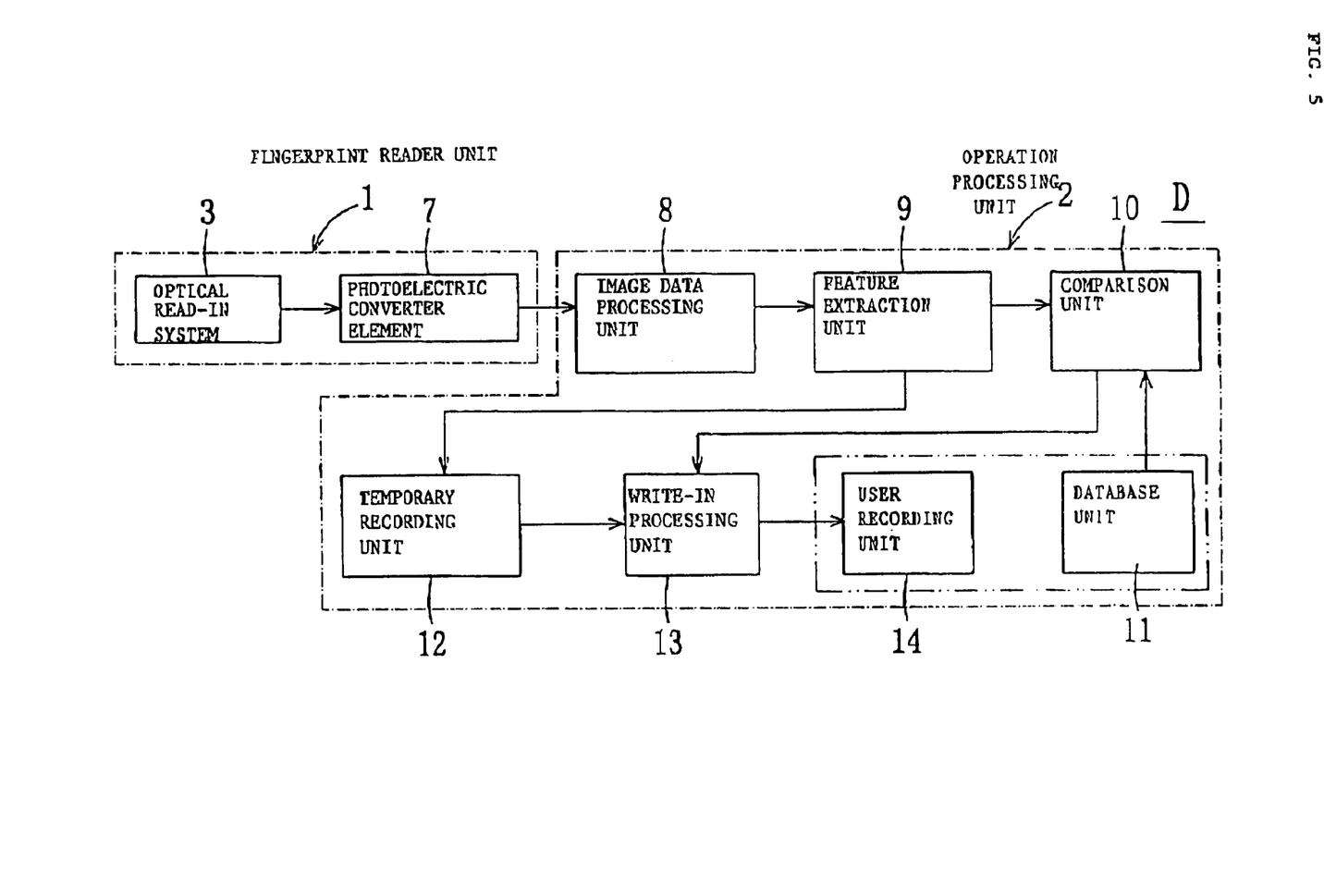
FIG. 5 is a block diagram of yet another fingerprint identification device to identify fingerprints according to a third preferred embodiment of this invention.

FIG. 5 is a block diagram of a fingerprint identification device D to identify fingerprints, according to a third preferred embodiment of this invention. In the fingerprint identification device D, the feature count data output by the feature extraction unit 9 is stored in the temporary recording unit 12. In the event that the prints do not match, the feature count data are saved in the user recording unit 14.

Since in this embodiment only the feature count data extracted by feature extraction unit 9 are stored in user recording unit 14, the memory consumption of user recording unit 14 is further reduced. Also, in this embodiment, it is possible to determine in the event of a malfunction whether the problem shows up in the feature count data extracted by feature extraction unit 9, or whether the problem lies in the matching processing executed by comparison unit 10. This simplifies the investigation of malfunctions. Since the feature count data can be used to distinguish one person from another, this scheme also provides a theft-deterrent effect.

In the embodiments discussed above, a single fingerprint pattern or set of feature count data is stored in a storage unit. However, if two or more patterns or sets of data were stored, the location of a malfunction could be determined with greater specificity.

Figure 6:
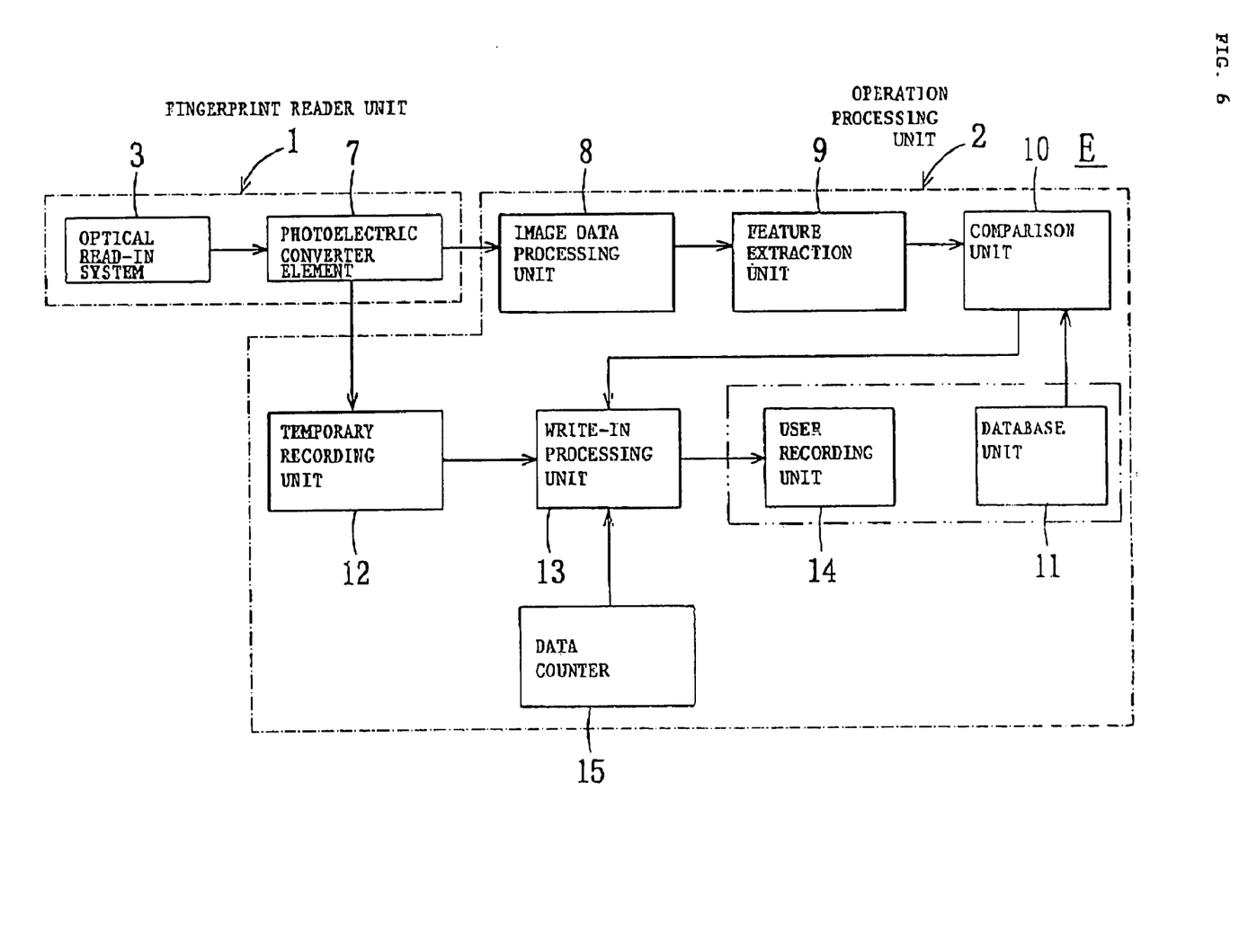
FIG. 6 is a block diagram of still another fingerprint identification device to identify fingerprints according to a fourth preferred embodiment of this invention.

FIG. 6 is a block diagram of a fingerprint identification device E to identify fingerprints, according to a fourth preferred embodiment of this invention. In the fingerprint identification device E, the fingerprint pattern output by the fingerprint reader 1 is stored in the temporary recording unit 12. This pattern may be either the one output by the image data processing unit 8 or the feature count data output by the feature extraction unit 9. If the comparison unit 10 finds that the prints do not match, write-in processing unit 13 retrieves the pattern stored in the temporary recording unit 12 and saves it in the user recording unit 14 along with the date and time data which is read out of a date counter 15 (generating/storing month, date and time data). Date counter 15 may be a counter built into a microprocessor used as the write-in processing unit 13. This counter, for example, adds the time which has elapsed since fingerprint identification device E was installed and began operating, and determines the date and time according to this elapsed time value.

Since in this embodiment the time that the prints are matched is recorded, the print patterns which are read can be inspected in the order that they were taken. For example, if i the density of the image is fading gradually over time, one can conclude that prism 5 of 0 fingerprint reader unit 1 is gradually getting dirtier. One can also determine whether the results of matching are different at night from what they are in the daytime. This feature further enhances the crime-deterrent effect of the fingerprint identification device.

The recording history stored in user recording unit 14 along with the fingerprint pattern need not be limited to date and time data. Power supply voltage or other similar information could also be recorded with the fingerprint.

Figure 7:
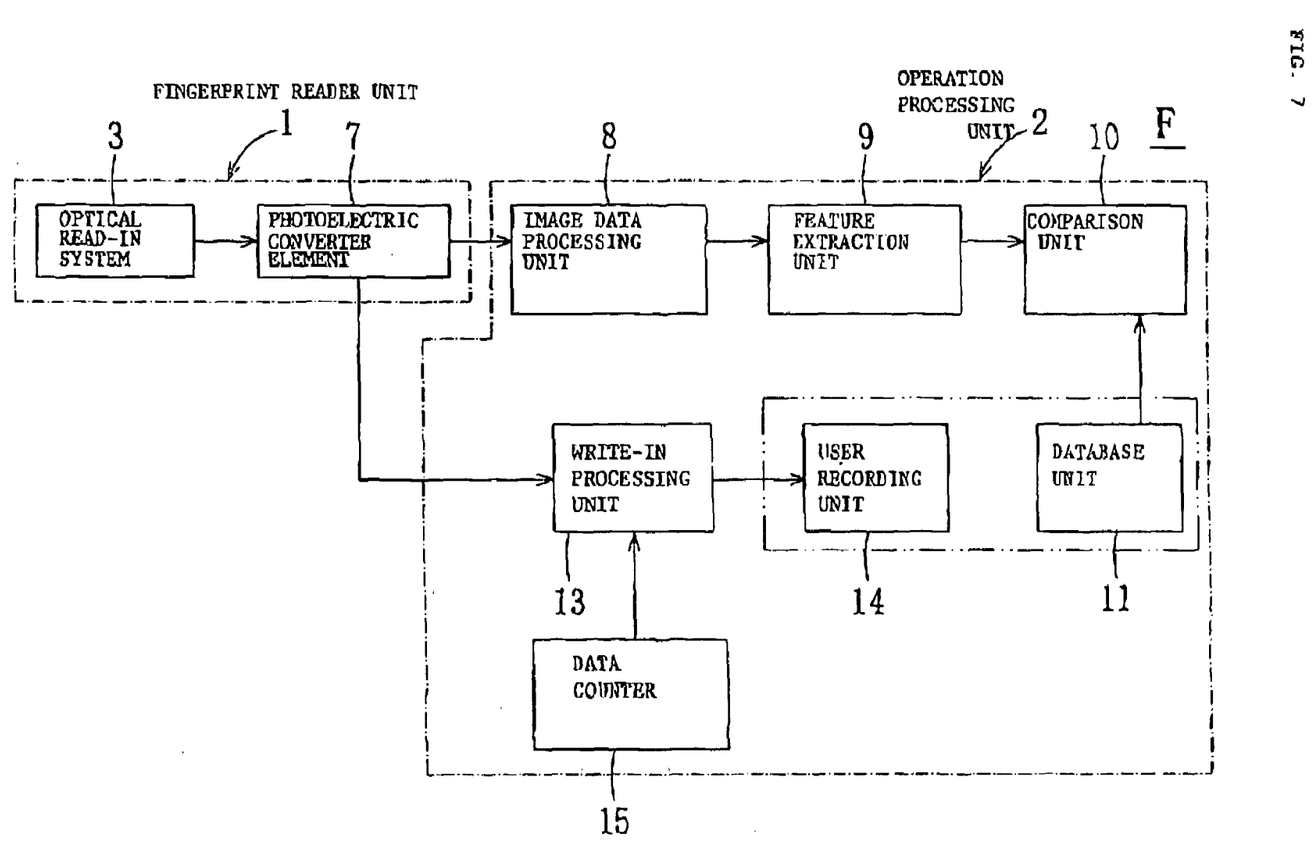
FIG. 7 is a block diagram of yet another fingerprint identification device to identify fingerprints according to a fifth preferred embodiment of this invention.

FIG. 7 is a block diagram of a fingerprint identification device F to identify fingerprints, according to a fifth preferred embodiment of this invention. In the fingerprint identification device F, the fingerprint pattern (and the date and time data) are stored in the user recording unit 14 regardless of the result of the matching done by comparison unit 10. In this embodiment, although user recording unit 14 requires a large memory capacity, the configuration of the device is simplified. There is also a large amount of data available to investigate the cause when a malfunction occurs, which makes it possible to determine in great detail the source of the problem.

Other embodiments of the invention will be apparent to those skilled in the art from a consideration of the specification and the practice of the invention disclosed herein. It is intended that the specification be considered as exemplary only, with the true scope and spirit of the invention being indicated by the following claims.

What is claimed is:

1. A fingerprint identification device to identify fingerprints, comprising:
    a fingerprint reader unit to read a fingerprint to be detected for outputting a fingerprint data;
    an image data processing unit to correct or compress said fingerprint data received from said fingerprint reader;
    a feature extraction unit to extract image features out of said corrected or compressed input fingerprint data received from said image data processing unit;
    a database unit to record a fingerprint database provided in advance;
    a fingerprint comparing unit that identifies said extracted image features received from said feature extraction unit by comparing with fingerprint data stored in said fingerprint database recorded in said database unit;
    a temporary recording unit to temporally record a temporary fingerprint data of said fingerprint; and
    a user recording unit to record said temporary fingerprint data transmitted from said temporary recording unit,
    wherein said temporary fingerprint data to be recorded in said temporary recording unit is said fingerprint data received from said fingerprint reader unit, and said temporary recording unit ignores said temporary fingerprint data in said temporary recording unit when said fingerprint comparing unit identifies said fingerprint, and further, said temporary recording unit automatically sends said temporary fingerprint data to said user recording unit for storing said temporary fingerprint data only when said fingerprint comparing unit does not identify said fingerprint, wherein said temporary fingerprint data enables narrowing down a location of malfunction in said fingerprint identification device.

2. The fingerprint identification device according to claim 1, wherein said temporary fingerprint data to be recorded in said temporary recording unit comprises said fingerprint data received from said fingerprint reader unit, and said temporary recording unit ignores said temporary fingerprint data when said fingerprint comparing unit identifies said fingerprint, and further said temporary recording unit automatically sends said temporary fingerprint data to said user recording unit for storing said temporary fingerprint data which includes a raw fingerprint data, only when said fingerprint comparing unit does not identify said fingerprint, in order to thereafter narrow down a location of malfunction in said fingerprint identification device.

3. The fingerprint identification device according to claim 1, wherein said temporary fingerprint data to be recorded in said temporary recording unit comprises said corrected or compressed fingerprint data received from said image data processing unit, and said temporary recording unit ignores said temporary fingerprint data when said fingerprint comparing unit identifies said fingerprint, and further said temporary recording unit automatically sends said temporary fingerprint data to said user recording unit for storing said temporary fingerprint data which includes said corrected or compressed fingerprint data resulting in compact data size, only when said fingerprint comparing unit does not identify said fingerprint, in order to thereafter narrow down a location of malfunction in said fingerprint identification device.

4. The fingerprint identification device according to claim 1, wherein said temporary fingerprint data to be recorded in said temporary recording unit comprises said extracted image features received from said feature extraction unit, and said temporary recording unit ignores said temporary fingerprint data when said fingerprint comparing unit identifies said fingerprint, and further said temporary recording unit automatically sends said temporary fingerprint data to said user recording unit for storing said temporary fingerprint data which includes said extracted image features resulting in compact data size, only when said fingerprint comparing unit does not identify said fingerprint, in order to thereafter narrow down a location of malfunction in said fingerprint identification device.

5. The fingerprint identification device according to claim 1, further comprising a date counter that provides a date record used to generate a recording history.

6. The fingerprint identification device according to claim 1, wherein said device is used for access control.

7. A method of identifying and recording fingerprints, comprising the steps of:
    recording reference fingerprints in advance in a database;
    inputting a fingerprint to be detected;
    processing said input fingerprint by correcting or compressing said input fingerprint;
    extracting image features out of said corrected or compressed input fingerprint;
    comparing said extracted image features to be detected to the reference fingerprints in the database;
    temporally recording a temporary fingerprint data which is either a raw fingerprint data, corrected or compressed fingerprint data, or said extracted image features; and
    automatically recording said temporary fingerprint data in a permanent user recording unit only when the input fingerprint to be detected does not match any of the reference fingerprints in the database wherein said temporary fingerprint data enables narrowing down a location of malfunction in said steps of said fingerprint identifying and recording method.

8. The fingerprint identification device according to claim 1, wherein said temporary fingerprint data stored in said temporary recording unit comprises a copy of the fingerprint data that is not used by the fingerprint comparing unit.

9. The method of identifying and recording fingerprints according to claim 7, wherein said temporary fingerprint data that is recorded comprises a copy of the fingerprint that is not used for comparing.

* * * * *